United States Patent [19]

Trademan

[11] 3,959,490

[45] *May 25, 1976

[54] GRANULAR CHLORDANE INSECTICIDAL PROCESS

[75] Inventor: Leo Trademan, Niles, Ill.

[73] Assignee: Velsicol Chemical Corporation, Chicago, Ill.

[ * ] Notice: The portion of the term of this patent subsequent to May 27, 1992, has been disclaimed.

[22] Filed: Dec. 20, 1974

[21] Appl. No.: 534,543

Related U.S. Application Data

[60] Division of Ser. No. 401,099, Sept. 26, 1973, Pat. No. 3,886,286, which is a continuation-in-part of Ser. No. 200,597, Nov. 19, 1971, abandoned.

[52] U.S. Cl. .................................................. 424/352
[51] Int. Cl.$^2$ ...................... A01N 9/30; A01N 9/32
[58] Field of Search ................................... 424/352

[56] References Cited
UNITED STATES PATENTS
2,760,900   8/1956   Glenn et al. ......................... 424/352

Primary Examiner—V. D. Turner
Attorney, Agent, or Firm—Robert J. Schwarz; Dietmar H. Olesch

[57] ABSTRACT

This invention discloses a free-flowing granular pesticide composition comprising an admixture of (a) a granular inert carrier having adsorbed thereon from about 20 to about 40 per cent by weight of the total composition of technical chlordane and (b) from about 0.5 to about 5.0 per cent by weight of the composition of magnesium stearate or aluminum stearate and a method for its preparation.

5 Claims, No Drawings

GRANULAR CHLORDANE INSECTICIDAL PROCESS

This application is a divisional of my copending application Ser. No. 401,099, filed Sept. 26, 1973, now U.S. Pat. No. 3,886,286 which is a continuation-in-part of application Ser. No. 200,597, filed Nov. 19, 1971, now abandoned.

This invention relates to granular pesticide formulations and more particularly relates to granular insecticide formulations containing a high concentration of toxicant which are relatively free of the tendency to form fines during their use in mechanical applicators.

Granular pesticide formulations are generally applied to the site of the pest infestation such as cultivated fields with a mechanical applicator. These mechanical applicators typically comprise an impeller positioned over an orifice at the bottom of a conical hopper. Rotation of the impeller delivers the pesticide granule to the orifice at a constant rate and thereby provides for a controlled application of the pesticide to the desired location.

While these mechanical applicators usually operate very satisfactorily, in some instances it has been found that when granular pesticide formulations having a high concentration of the active ingredient are used, clogging of the applicator orifice and destruction of the impeller results. This problem is particularly acute when the active ingredient is technical chlordane and the concentration exceeds about 20 per cent.

While the exact reason for this clogging is not fully understood, it is believed that the formation of fines having inferior adsorbent properties rather than the parent granules is the cause of the clogging. Mechanical friction of the impregnated granules produces the fines which due to their decreased adsorbtive capacity become compactible when subjected to mechanical forces. Such compacting takes place at the orifice of the pesticide applicator upon exertion of mechanical forces by the impeller in the vicinity of the orifice. This compacting results in the buildup of a hard deposit causing clogging of the orifice and damage to the impeller.

It has now been found that pesticide granules and particularly chlordane granules having a high concentration of toxicant can be obtained which do not cause clogging or the formation of fines when used in mechanical pesticide applicators. More particularly, it has been found that a nonclogging granular chlordane formulation having a technical chlordane content of from about 20 to about 40 per cent by weight can be obtained by admixing the granules with magnesium stearate or aluminum stearate.

Thus, one embodiment of this invention resides in a free-flowing granular pesticide composition comprising an admixture of (a) a granular inert carrier having adsorbed thereon from about 20 to about 40 per cent by weight of the total composition of technical chlordane and (b) from about 0.5 to about 5.0 per cent by weight of the composition of magnesium stearate or aluminum stearate.

The granular inert carrier useful for preparing the compositions of this invention can comprise such materials as attapulgite, montmorillonite or diatomaceous earth having a particle size range of from about 0.3 to about 3.0 mm.

Chlordane is the approved name for the compound 1,2,4,5,6,7,8,8-octachloro-4,7-methano-3a, 4,7,7a-tetrahydroindane.

Technical chlordane is a mixture of insecticidal components including chlorinated addition and substitution derivatives of 1,2,4,5,6,7,8,8-octachloro-4,7-methano-3a,-4,7,7a-tetrahydroindane. The chlorine content is between about 64 and 67 per cent. The principal components are isomers of chlordane, isomers of chlordene, heptachlor and nonachlor. Technical chlordane conforms to the biological, chemical and physical properties of Reference Technical Chlordane. Technical chlordane is a commercial insecticide useful in agriculture, turf and households for the control of insects. Among insects controlled by technical chlordane are ants, boxelder bugs, centipedes, earwigs, clothes moths, mosquitos, spiders, ticks, crickets, carpet beetles, cockroaches, flees, silverfish, scorpions, wasps, corn rootworm, corn root aphids, cutworms, white grubs, wireworms, termites, Japanese beetles, mole crickets, sod webworms, and others.

Magnesium and aluminum stearate are white amorphous solids of the formula $Mg(C_{17}H_{35}CO_2)_2$ and $Al(C_{17}H_{35}CO_2)_3$, respectively. When used in the compositions of this invention, they are preferably used as finely divided powders having a particle size capable of passing through a 100 mesh screen. The exact amount of magnesium or aluminum stearate used in the present compositions is not critical provided that at least about 0.5 per cent by weight of the total composition is used. Generally, an amount ranging from about 0.5 to about 5.0 per cent can be suitably employed.

The free-flowing granular pesticide compositions of this invention can be readily prepared by incorporating the magnesium of aluminum stearate with the technical chlordane impregnated granular carrier. This incorporation can be carried out in conventional blending equipment such as a tumbler blender, ribbon blender, or the like.

The magnesium or aluminum stearate must be applied to the granules only after they have been impregnated with the technical chlordane and after the technical chlordane has been completely adsorbed into the granule in order to obtain the compositions of this invention. Thus, the incorporation of the aluminum or magnesium stearate will be the last step in preparing the present composition. It is preferred to permit the technical chlordane impregnated granules to age for a period of about three days prior to applying the magnesium or aluminum stearate.

The technical chlordane impregnated inert carrier can be readily prepared by standard techniques such as spraying liquid technical chlordane or a solution thereof unto the granulated carrier until the desired concentration has been reached.

A stabilizer can be incorporated into the formulation to prevent the carrier from deteriorating the technical chlordane. Exemplary stabilizers which can be used are ethylene glycol, propylene glycol, diethylene glycol and triethylene glycol. Such stabilizers can be used in an amount ranging from about 1 to about 10 per cent by weight of the carrier and preferably from about 2 to about 8 per cent by weight.

The preparation of the compositions of this invention are more specifically illustrated in the following examples.

EXAMPLE 1

Preparation of a Free-Flowing Attapulgite Granule

Granular attapulgite capable of passing through a 20 mesh screen (2000 grams) is charged into a tumbler blender equipped with internal spraying nozzles. Technical chlordane (1000 grams) is heated to a temperature of about 180° F. and is sprayed unto the attapulgite while tumbling in the blender. After the spraying is completed, tumbling is continued for a period of about 7 minutes to insure uniformity. After this time the granules are permitted to stand for 3 days. Powdered magnesium stearate (30 grams) is then added to the impregnated granules and the mixture is blended for a period of about 6 minutes or until a uniform blend is obtained to yield the desired free-flowing composition of this invention.

EXAMPLE 2

Preparation of a Free-Flowing Diatomaceous Earth Granule

Granular diatomite capable of passing through a 30 mesh screen (4000 grams) is charged into a tumbler blender equipped with internal spraying nozzles. A solution of technical chlordane (1000 grams) in mineral spirits (300 grams) is sprayed unto the diatomite while tumbling in the blender. After the spraying is completed, tumbling is continued for a period of about 10 minutes to ensure uniformity and complete adsorption of the technical chlordane. After this time, the granules are allowed to stand for a period of about 4 days. Powdered aluminum stearate (25 grams) is then added to the impregnated granules and the mixture is blended for a period of about 10 minutes to yield a desired free-flowing composition of this invention.

EXAMPLE 3

Preparation of a Free-Flowing Montmorillonite Granule

Granular montmorillonite capable of passing through a 10 mesh screen (6000 grams) is charged into a tumbler blender equipped with internal spraying nozzles. Technical chlordane (4000 grams) is heated to a temperature of about 200° F. and is sprayed unto the montmorillonite while tumbling in the blender. After the spraying is completed, tumbling is continued for a period of about 5 minutes to ensure uniformity and complete adsorption of the technical chlordane. After this time, the granules are permitted to stand for 3 days. Powdered magnesium stearate (500 grams) is then added to the impregnated granules and the mixture is blended for a period of about 10 minutes to yield the desired free-flowing composition of this invention.

EXAMPLE 4

Preparation of a Free-Flowing Attapulgite Granule

Granular attapulgite (6670 grams) is charged into a tumbler blender equipped with internal spraying nozzles. Technical chlordane (3330 grams) and diethylene glycol (40 grams) are combined and heated to a temperature of about 200° F. The mixture is sprayed upon the attapulgite granules while tumbling in the blender. After spraying is completed, tumbling is continued for a period of about 7 minutes to ensure uniformity and total adsorption of the technical chlordane and glycol. After this time the granules are allowed to stand for about 3 days. Powdered magnesium stearate having a particle size of which 99 percent can pass through a 325 mesh U.S. Standard sieve (100 grams) is then added to the impregnated granules and the mixture is blended for a period of about 10 minutes to yield the desired composition of this invention.

The effectiveness of the compositions of this invention was demonstrated in an experiment wherein the tendency to form fines of various granular formulations was determined upon passing through a mechanical pesticide applicator. In this experiment a granular technical chlordane composition prepared in accordance with Example 4 was compared with an indentical composition which did not contain magnesium stearate. The amount of fines was determined by sieve analysis upon measuring the weight percent retained in various mesh screens. Each of the formulations was analyzed before and after having passed through the applicator. A total of ten pounds of each composition was passed through the applicator. The results of this experiment are presented in Table I.

TABLE I

Weight Per Cent of Composition Retained in Standard Sieves Pesticide Composition*

| Sieve Size | No. 1 | No. 2 | No. 3 | No. 4 |
|---|---|---|---|---|
| 16 Mesh | 2.0 | 0.57 | 2.0 | 2.8 |
| 40 Mesh | 96.5 | 98.23 | 88.04 | 96.3 |
| 100 Mesh | 1.0 | 1.04 | 7.0 | 0.8 |
| Bottom Pan | 0.5 | 0.16 | 3.0 | 0.1 |

*Composition No. 1 = Product of Example 4 having passed through applicator.
Composition No. 2 = Product of Example 4 without having passed through applicator.
Composition No. 3 = Product of Example 4 without magnesium stearate, having passed through applicator.
Composition No. 4 = Product of Example 4 without magnesium stearate, without having passed through applicator.

It can be seen from the date presented in the above table that the composition prepared without magnesium stearate resulted in increase of 9.1 percent of fines (particles retained on 100 mesh screen + particles in bottom pan) upon passing through the applicator while the composition prepared with magnesium stearate resulted in an increase of only 0.3 percent upon the same treatment.

I claim:

1. A method for preparing a free-flowing granular technical chlordane insecticidal composition which comprises incorporating from about 0.5 to about 5.0 percent by weight of the composition of magnesium stearate or aluminum stearate onto a granular inert carrier having adsorbed thereon an insecticidally-effective amount of technical chlordane.

2. The method of claim 1 wherein the carrier is attapulgite.

3. The method of claim 1 wherein the carrier is montmorillonite.

4. The method of claim 1 wherein the carrier is diatomaceous earth.

5. The method of claim 1 wherein the compositions contain as an additional component from about 1 to about 10 percent by weight based on the inert carrier of a stabilizer selected from the group consisting of ethylene glycol, propylene glycol, diethylene glycol and triethylene glycol.

* * * * *